(12) United States Patent
Pinter (10) Patent No.: US 10,067,069 B2
(45) Date of Patent: Sep. 4, 2018

(54) MACHINE VISION SYSTEMS INCORPORATING POLARIZED ELECTROMAGNETIC RADIATION EMITTERS

(71) Applicant: Smart Vision Lights, Muskegon, MI (US)

(72) Inventor: Gilbert Pinter, Muskegon, MI (US)

( * ) Notice: Subject to any disclaimer, the term of this patent is extended or adjusted under 35 U.S.C. 154(b) by 0 days.

(21) Appl. No.: 15/455,868

(22) Filed: Mar. 10, 2017

(65) Prior Publication Data

US 2017/0262674 A1 Sep. 14, 2017

Related U.S. Application Data

(60) Provisional application No. 62/307,300, filed on Mar. 11, 2016.

(51) Int. Cl.
*G06K 7/10* (2006.01)
*G06K 7/14* (2006.01)
*G01N 21/88* (2006.01)

(52) U.S. Cl.
CPC ..... *G01N 21/8806* (2013.01); *G06K 7/10722* (2013.01); *G06K 7/1413* (2013.01); *G06K 7/1417* (2013.01)

(58) Field of Classification Search
CPC ............. G06K 7/10722; G06K 7/1413; G06K 7/1417; G01N 21/8806
See application file for complete search history.

(56) References Cited

U.S. PATENT DOCUMENTS

| | | | | |
|---|---|---|---|---|
| 3,704,937 A | * | 12/1972 | Waring | G02F 1/05 359/246 |
| 3,806,903 A | * | 4/1974 | Myer | G06F 7/026 359/107 |
| 4,603,262 A | * | 7/1986 | Eastman | G06K 7/10881 235/462.06 |
| 4,720,706 A | * | 1/1988 | Stine | G09G 3/20 345/690 |
| 5,010,241 A | * | 4/1991 | Butterworth | G06K 7/10594 235/454 |

(Continued)

FOREIGN PATENT DOCUMENTS

JP 02075906 A * 3/1990
JP 2002358684 A * 12/2002

OTHER PUBLICATIONS

Thorlabs, https://www.thorlabs.com/newgrouppage9.cfm?objectgroup_id=10813, Liquid Crystal Polarization Rotators, 1999-2018.*

(Continued)

*Primary Examiner* — Daniel Walsh
(74) *Attorney, Agent, or Firm* — James E. Shultz, Jr.

(57) ABSTRACT

Machine vision systems are provided. More specifically, machine vision systems are provided that incorporate polarized illumination and detection. Polarized electromagnetic radiation may be used to reduce glare and enable increased flashing speed in machine vision detection systems. Ultra-high power light sources, heat tolerant polarizing media and optical-path systems may be coupled with ultra-high speed flashing systems to enable increased web-speed while maintaining necessary accuracy in web-scanning operations.

20 Claims, 10 Drawing Sheets

(56) References Cited

U.S. PATENT DOCUMENTS

| | | | | |
|---|---|---|---|---|
| 5,181,222 A * | 1/1993 | Duarte | ............... | H01S 3/08004 372/102 |
| 7,619,804 B1 * | 11/2009 | Demiryont | ............ | G02F 1/1523 359/265 |
| 9,506,871 B1 * | 11/2016 | Flock | ................ | G01N 21/8806 |
| 9,854,180 B2 * | 12/2017 | Davis | .................... | H04N 5/238 |
| 2003/0058408 A1 * | 3/2003 | Magarill | ............... | G02B 5/3033 353/20 |
| 2004/0258106 A1 * | 12/2004 | Araujo | ................... | H01S 3/025 372/9 |
| 2005/0046848 A1 * | 3/2005 | Cromwell | ......... | G01N 21/6408 356/417 |
| 2006/0044628 A1 * | 3/2006 | Huang | .............. | H04N 1/02865 358/475 |
| 2006/0132066 A1 * | 6/2006 | Winer | ................ | G09G 3/3406 315/363 |
| 2007/0188425 A1 * | 8/2007 | Saccomanno | ....... | G09G 3/3406 345/82 |
| 2007/0201136 A1 * | 8/2007 | Myrick | ................. | G01N 21/55 359/578 |
| 2007/0242354 A1 * | 10/2007 | Takahashi | ........... | G11B 7/1365 359/489.06 |
| 2008/0000976 A1 * | 1/2008 | Thomas | .................. | G06K 7/10 235/454 |
| 2008/0266662 A1 * | 10/2008 | Perkins | ............... | G02B 5/1814 359/485.05 |
| 2008/0316303 A1 * | 12/2008 | Chiu | ...................... | G09G 3/003 348/51 |
| 2010/0004875 A1 * | 1/2010 | Urano | ................ | G01N 21/4738 702/40 |
| 2010/0051808 A1 * | 3/2010 | Zeman | ................ | A61B 5/0059 250/330 |
| 2011/0090321 A1 * | 4/2011 | Nakagawa | ............ | G09G 3/003 348/51 |
| 2011/0228510 A1 * | 9/2011 | Park | ........................ | G02B 5/23 362/19 |
| 2011/0248086 A1 * | 10/2011 | Droemer | ............ | G06K 7/10702 235/455 |
| 2012/0176676 A1 * | 7/2012 | Sakamoto | ........... | G02B 5/3058 359/485.05 |
| 2013/0083324 A1 * | 4/2013 | Wilhelm | .............. | G01N 21/274 356/431 |
| 2014/0184800 A1 * | 7/2014 | Hirai | ................... | G01N 21/958 348/148 |
| 2014/0260640 A1 * | 9/2014 | Sullivan | ............. | G01N 29/2418 73/655 |
| 2014/0264979 A1 * | 9/2014 | Park | .................... | B29C 47/0021 264/1.34 |
| 2014/0300805 A1 * | 10/2014 | Davis | .................... | H04N 5/238 348/362 |
| 2015/0036030 A1 * | 2/2015 | Kido | ....................... | H04N 5/332 348/281 |
| 2015/0115032 A1 * | 4/2015 | Chi | ..................... | G06K 7/10831 235/455 |
| 2016/0027963 A1 * | 1/2016 | Jun | ........................ | H01L 33/06 257/13 |
| 2017/0262674 A1 * | 9/2017 | Pinter | ................. | G01N 21/8806 |

OTHER PUBLICATIONS

Thorlabs, https://www.thorlabs.com/newgrouppage9.cfm?objectgroup_id=6179, Half-Wave Liquid Crystal Variable Retarders/Wave Plates, 1999-2018.*

OSA Publishing, https://www.osapublishing.org/ol/abstract.cfm?uri=ol-30-2-195, High Performance nanowire-grid polarizers, 2005.*

* cited by examiner

MACHINE VISION SYSTEMS INCORPORATING POLARIZED ELECTROMAGNETIC RADIATION EMITTERS

CROSS-REFERENCE TO RELATED APPLICATIONS

The present application claims benefit of priority, under 35 U.S.C. § 119(b), to U.S. Provisional Patent Application Ser. No. 62/307,300, entitled THE USE OF POLARIZATION IN ELECTROMAGNETIC RADIATION DETECTION SOURCES USED FOR OPTICAL SCANNING IN MACHINE VISION APPLICATIONS, filed Mar. 11, 2016, the disclosure of which is incorporated herein in its entirety by reference.

TECHNICAL FIELD

This present disclosure generally relates to machine vision systems. More specifically, the present disclosure relates to machine vision systems incorporating polarized illumination and detection.

BACKGROUND

Machine vision systems are becoming common in various manufacturing, retail, distribution, transportation, and related facilities. Generally, a machine vision system includes at least one illumination source for emitting light, and at least one light detector (e.g., light sensor, camera, etc.) for detecting light emitted from the at least one illumination source and/or light that is reflected from an object (e.g., a bar code, a label, etc.).

Often times, machine vision systems experience false light detection because, for example, ambient lighting is mistakenly detected as light emitted from a light source of the machine vision system.

What is needed is an illumination source, for use within a machine vision system, that is distinguishable from ambient lighting.

SUMMARY

A machine vision system may include at least one illumination source for emitting light. The machine vision system may also include at least one polarizer for polarizing the light emitted from the at least one illumination source. The machine vision system may further include at least one optical element for focusing the light emitted from the at least one illumination source. The machine vision system may yet further include at least one light detector, wherein the at least one light detector is configured to detect polarized light.

In another embodiment, an illumination source for machine vision systems may include at least one illumination source for emitting light. The illumination source for machine vision systems may also include at least one polarizer for polarizing the light emitted from the at least one illumination source. The illumination source for machine vision systems may further include at least one optical element for focusing the light emitted from the at least one illumination source.

In a further embodiment, an illumination source for machine vision systems may include at least one illumination source for emitting light. The illumination source for machine vision systems may also include at least one polarizer for polarizing the light emitted from the at least one illumination source. The illumination source for machine vision systems may further include at least one optical element for focusing the light emitted from the at least one illumination source. The illumination source for machine vision systems may yet further include at least one feedback control link which enables an associated illumination system to control at least one of: an illumination intensity of emitted light, a spectral property of emitted light, a duration of an on-time of the at least one illumination source, a frequency of flashing on and off of the at least one illumination source, or a plane of polarization of emitted light.

These and other features, advantages, and objects of the present invention will be further understood and appreciated by those skilled in the art by reference to the following specifications, preferred embodiments, claims, and drawings.

DETAILED DESCRIPTION

Machine vision systems are provided. More specifically, machine vision systems are provided that incorporate polarized illumination and detection. Polarized electromagnetic radiation sources are provided that may enable associated machine vision systems to distinguish between ambient light and light emitted by light sources incorporated within the machine vision systems. Polarized electromagnetic radiation sources are provided that may reduce glare and may enable increased flashing speed in machine vision detection systems. Ultra-high power light sources, heat tolerant polarizing media and optical-path systems may be coupled with ultra-high speed flashing systems to enable increased web-speed of associated production lines while maintaining necessary accuracy in associated web-scanning operations.

Polarized light or other photonic, electromagnetic energy sources of the present disclosure may be used for line-scanning within machine vision, particularly as such scanning is used in high speed manufacturing lines for quality inspection and quality control applications. Examples are found in such applications as raw materials grading and sorting, web processing of materials, identification of non-conformance in manufactured goods, and applications for use incoming materials quality control, in-process control, finished goods inspection, inventory control, barcode readers, quick response (QR) code readers, supply chain quality management operations, etc.

The term "polarization," as used herein, is in context of electromagnetic radiation to refer to uniform directional alignment of associated vector components of photons making up emitted light and all other electromagnetic radiation. Light (and all other wavelengths of electromagnetic radiation—such as photons) may be characterized in contemporary physics as having five distinct and measurable vector components of: 1.) electric displacement, 2.) magnetic induction, 3.) electric field intensity, 4.) magnetic field intensity, and 5.) electric current intensity. Sun Light, for example, may include a random distribution of these vector components with an average power of 1,000 Watts per Square meter on a surface of Earth.

Polarized Light, as a special case, consists of light which may be treated so as to have a majority of its photon vectors parallel in a plane which is in the direction of its travel. Polarized light may be "coherent and monochromatic" if it is generated by a L.A.S.E.R. but mixed spectra-colors may be polarized through diffraction, reflection, or transmission through a polarizing media, such that associated field vectors are parallel in a plane or parallel in a curvilinear (either rotating or twisting) propagation path.

A light source for use in machine vision may include a conventional source of non-polarized illumination, and include a nano-wire diffraction grid to polarize the light source's illumination so as to oriented photon field component in a preferential plane. Such light sources may include at least one focusing lens which may be common to line scanning in machine vision applications.

A polarizing transmission media may be used to polarize light emitted from an associated light source. Such polarizing transmission media may use chemicals which refract light in a controlled manner so as to polarize the light for use in, for example, line scanning applications. For example, polymer polarizing molecules or crystalline materials may be incorporated to polarize light in a transmission media.

A thin-film polarizing coating may be applied to at least one lens within an illumination system using coatings methods such as, for example, chemical vapor deposition methods, or plasma vapor deposition technologies. Multiple layers of thin-film polarizing coatings may be applied to create optical filters which may screen out at least one predetermined wavelength of light which may enhance an associated electromagnetic spectra for a reflected image presented to a high-speed digital camera and associated imaging software. Such a polarizing and filtering system may improve an optical signal to noise ratio and may result in higher speed and greater accuracy of the line scanning process.

A single or multi-layer photo-chromic coating may be deposited on at least one lens system within a light source of the present disclosure, which may vary an amount (boost or attenuate) of polarization used in the light source ("light" here applying to both visible or not visible electromagnetic radiation), and/or may rotate a plane of polarization selectively as a response from external control mechanisms or in response to external changes in scanned objects (environmental conditions or the identification of otherwise invisible markings on scanned objects). Filtering and wave controlling functions may be controlled electronically and/or with fast response times (typically in nano-seconds).

National or corporate security may require identification on scanned items which are not intended for general identification and disclosure. In a distribution setting such items may be, using the illumination sources of the present disclosure, identified by polarized scanning and diverted to a secure loading station while being invisible to unauthorized line operators.

A prismatic element may be used within an illumination source of the present disclosure to polarize and/or create a spread-line spectrum for multiple scanning events based on, for example, use of color filters on a camera or electronic digital control of color recognition within the camera. This may create confirming, multiple scanning events in one pass of the scanned object based on color recognition in the camera.

A linear illumination source, using a plurality of high powered L.E.D. sources, high-heat tolerant nano-wire polarizing grids, and high-heat tolerant (e.g., silicone) lenses may form a high speed web-scanning (bar-type) illumination source which may be used either in a strobe-mode, for discrete imaging, or in continuous wave mode, with high speed cameras, to allow web-speeds to increase without losing quality control effectiveness. Web-scanning cameras may be incorporated into an associated machine vision system that are capable of image processing at up to 10,000 frames per second, thereby, creating a strobe frequency and/or polarized light characteristics to make accurate and meaningful assessments of a web-quality in real time.

Figure 1:
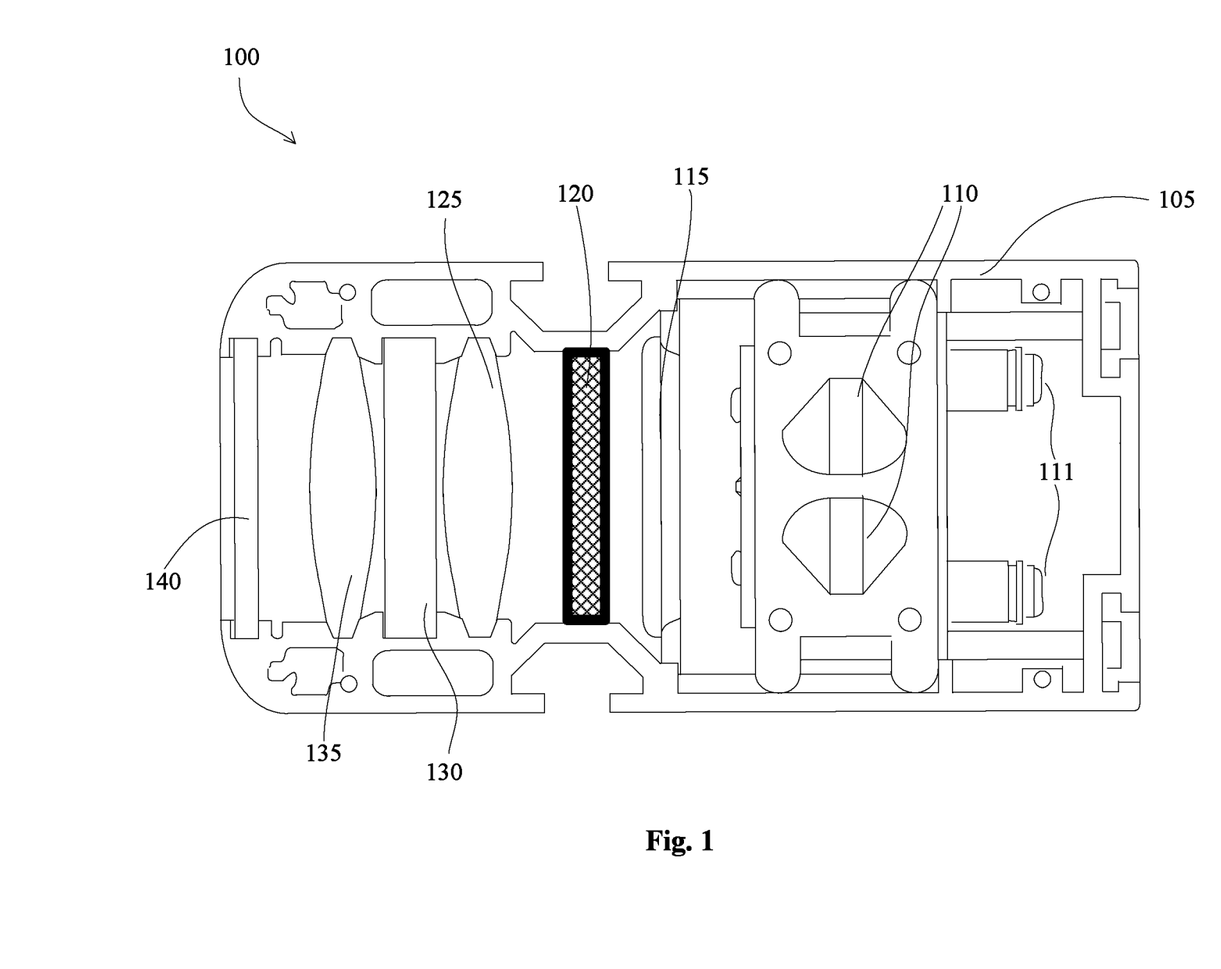
FIG. 1 depicts an example illumination source for a machine vision system.

Turning to FIG. 1, an illumination source 100 may include at least one light source 110 having associated electrical connections 111. The light source 110 may emit un-polarized light. The illumination source 100 may also include a transmission polarizing element 120 with dual symmetrical focusing lenses 125, 135. The illumination source 100 may further include an un-polarized optical element 115, a light filter 130 and a cover 140. The illumination source 100 may emit focused and polarized light. The term "light," as used herein, is used to include electromagnetic radiation (e.g., photons) whether in a visible spectrum or wavelengths above or below a range of human sight. The illumination source 100 may be an intermittent strobe or continuous wave as may fit particular machine vision system requirements. The light sources 110 with electrical connections 111, the un-polarized optical element 115, the light filter 130, the dual symmetrical focusing lenses 125, 135, the transmission polarizing element 120, and the cover 140 may be secured in position relative one another via a housing 105.

Figure 2:
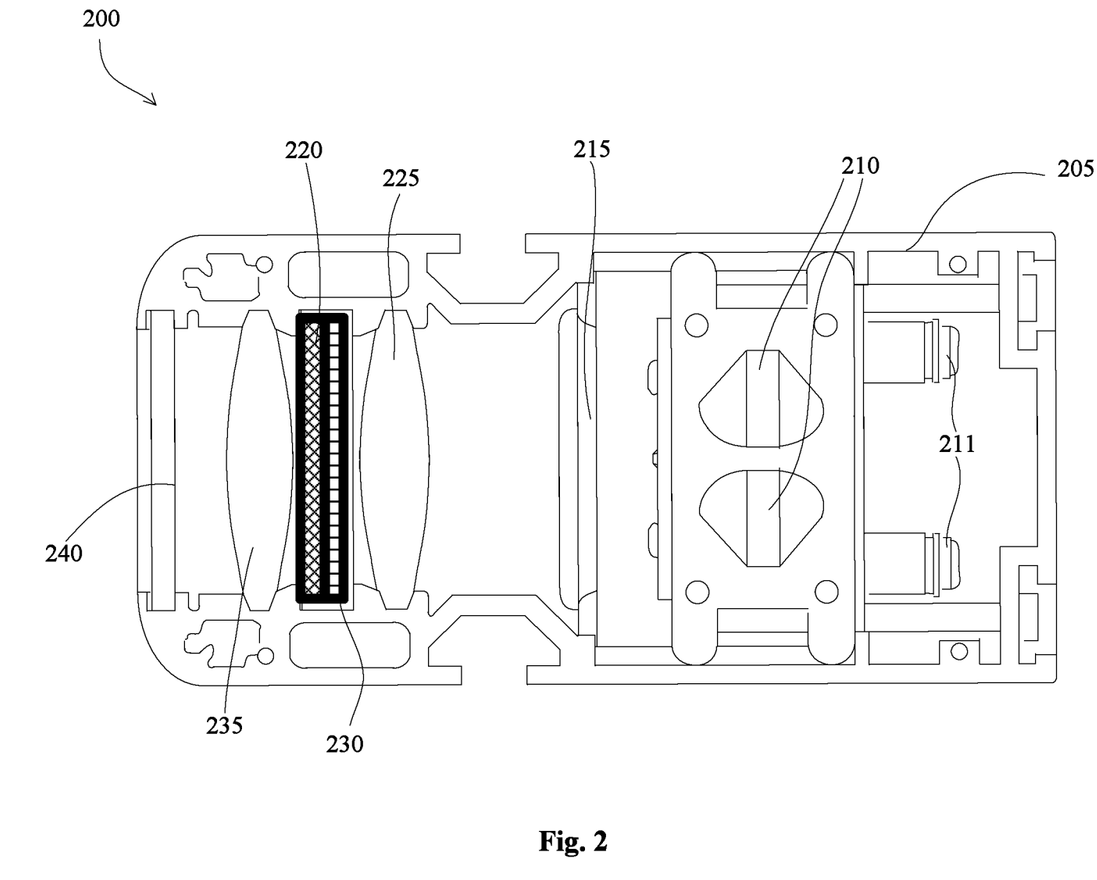
FIG. 2 depicts an example illumination source for a machine vision system.

With reference to FIG. 2, an illumination source 200 may include at least one light source 210, having electrical connections 211, that may emit, for example, collimated un-polarized light. The collimated un-polarized light may be propagating through a transmission polarizing medium 220, an active filtering medium 230, and twin focusing lenses 225, 235. The illumination source 200 may emit focused and filtered polarized light through a cover 240. The illumination source 200 may further include an un-polarized optical element 215. The light sources 210 with electrical connections 211, the un-polarized optical element 215, the filtering medium 230, the transmission polarizing medium 220, the twin focusing lenses 225, 235, and the cover 240 may be secured in position relative one another via a housing 205.

Figure 3:
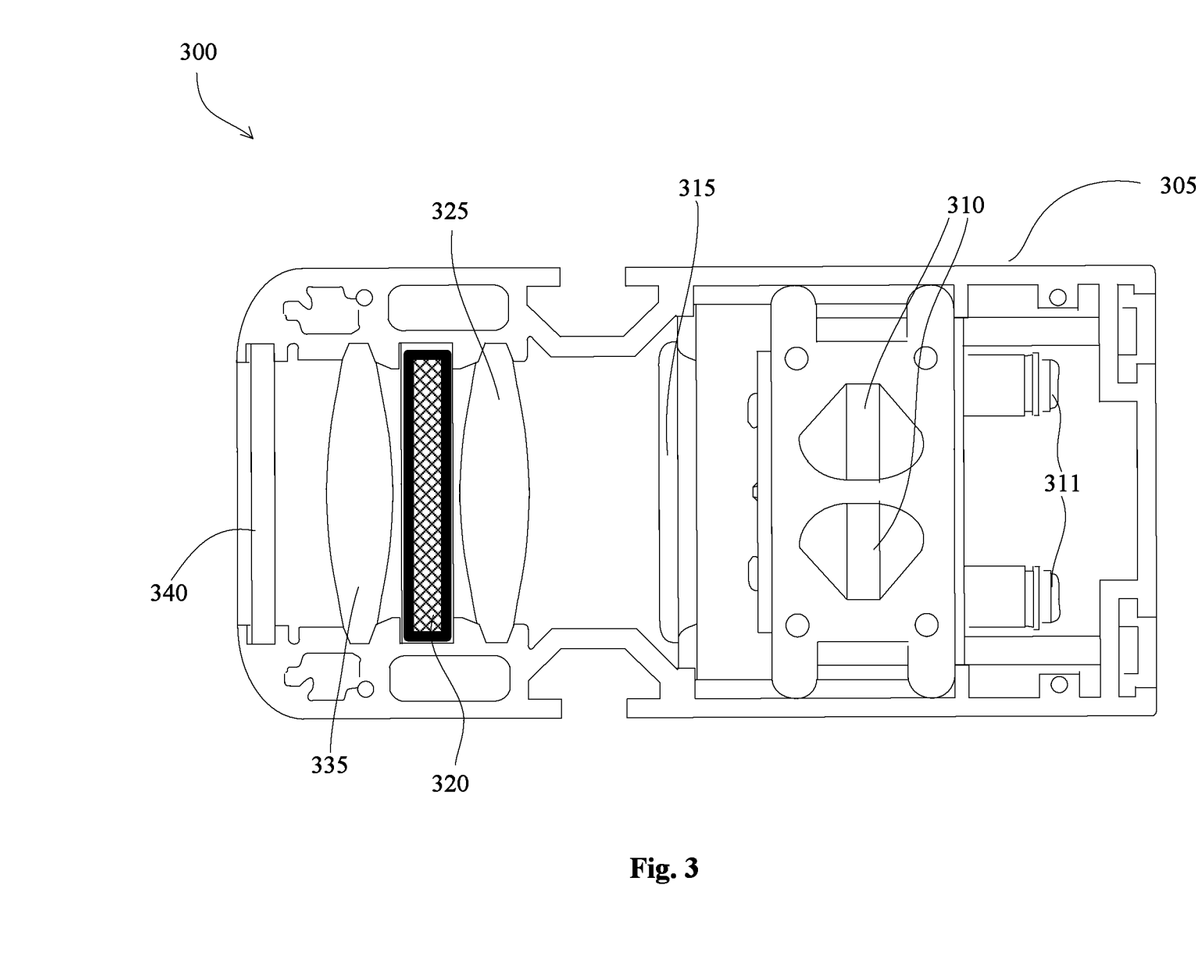
FIG. 3 depicts an example illumination source for a machine vision system.

Turning to FIG. 3, an illumination source 300 may be include at least one light source 310, having electrical connections 311, that may emit, for example, collimated un-polarized light. The collimated un-polarized light may be propagating through a nano-wire polarizing grid 320 and twin focusing lenses 325, 335. The illumination source 300 may emit focused polarized light through a cover 340. The illumination source 300 may further include an un-polarized optical element 315. The light sources 310 with electrical connections 311, the un-polarized optical element 315, the twin focusing lenses 325, 335, the nano-wire polarizing grid 320, and the cover 340 may be secured in position relative one another via a housing 305. The nano-wire polarizing grid, used as a transmission polarizing element, may, for example, be employed in high-heat environments. High-heat may be created, for example, from high average power necessary for illumination in ultra high speed imaging.

Figure 4:
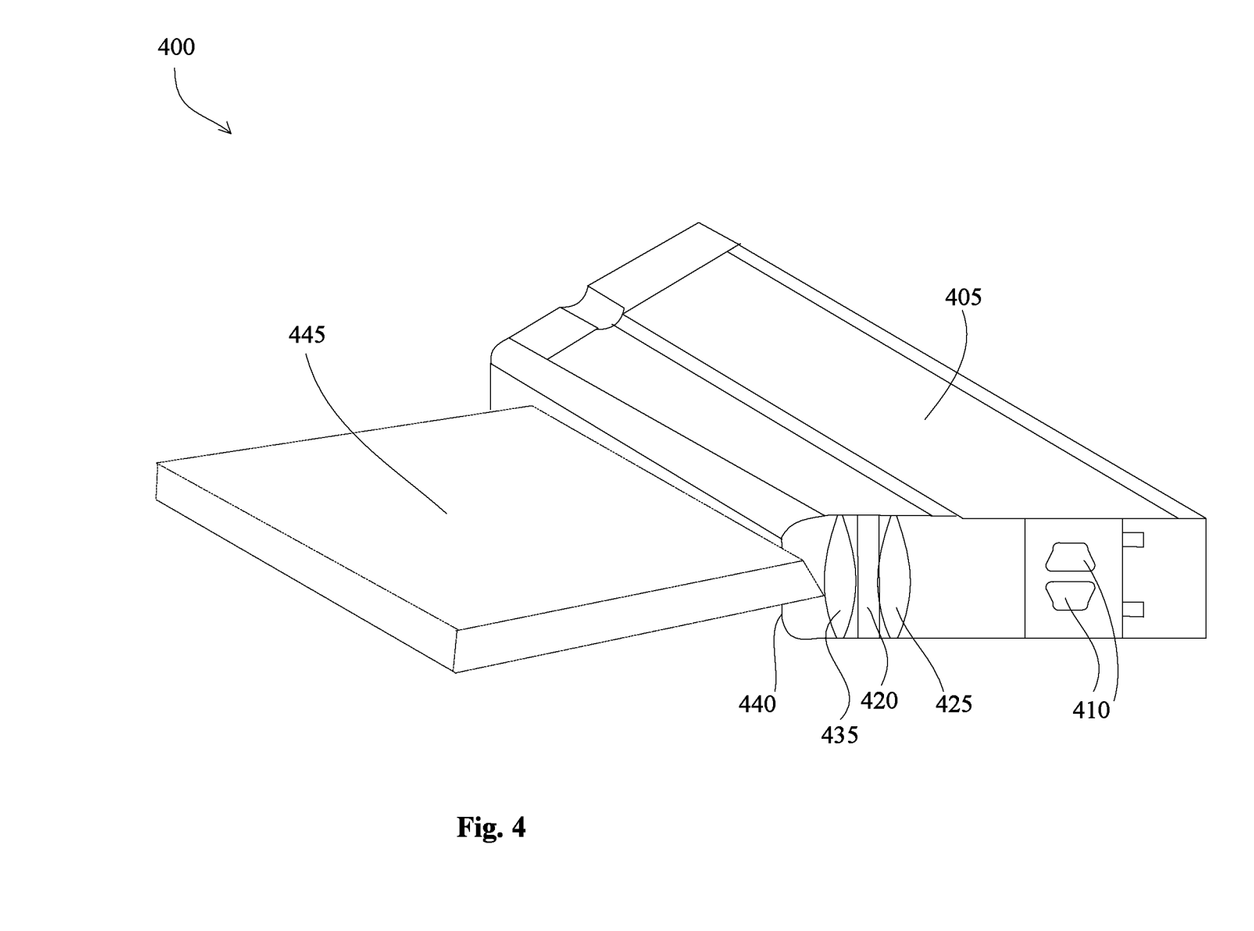
FIG. 4 depicts an example illumination source for a machine vision system.
Figure 5A:
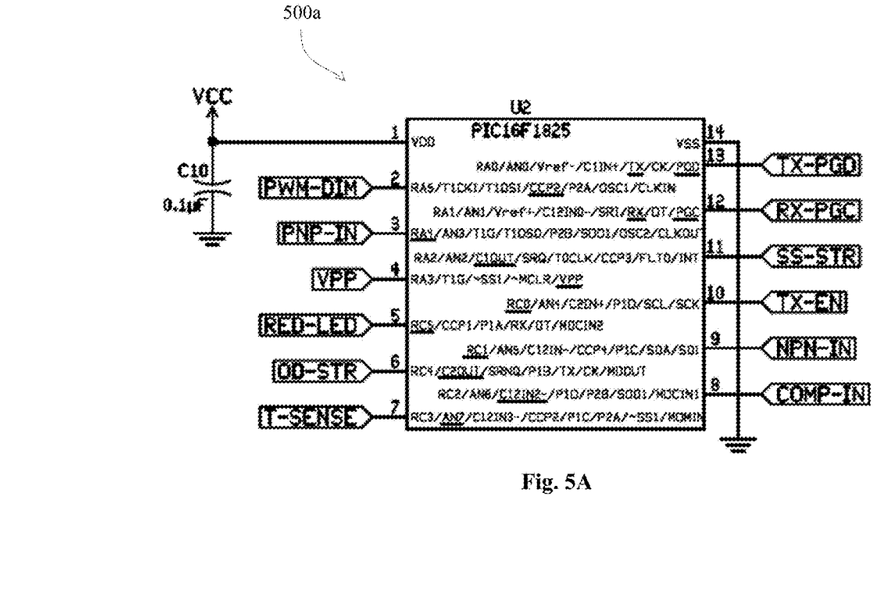
FIGS. 5A-H, J and K depict an example control for an illumination source for a machine vision system.
Figure 5B:
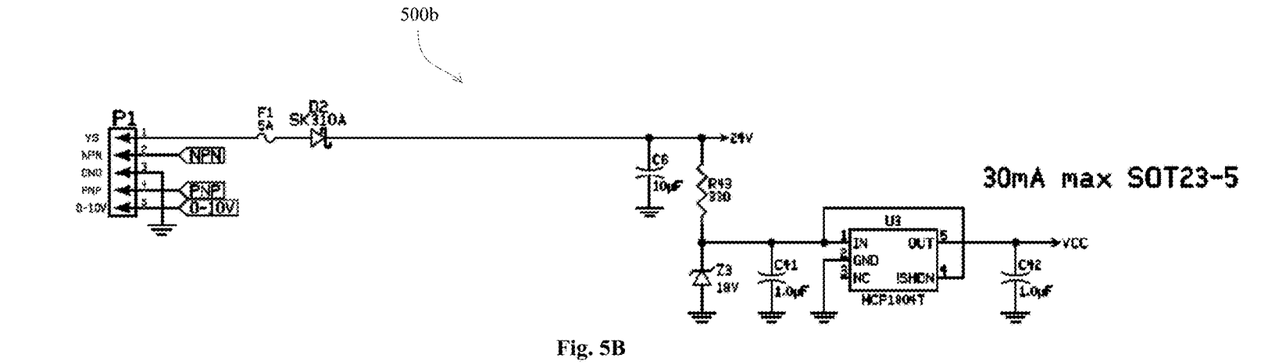
Figure 5C:
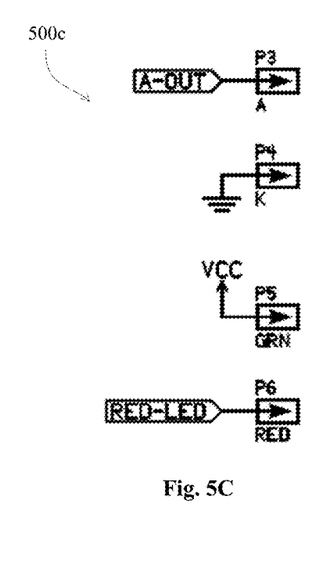
Figure 5D:
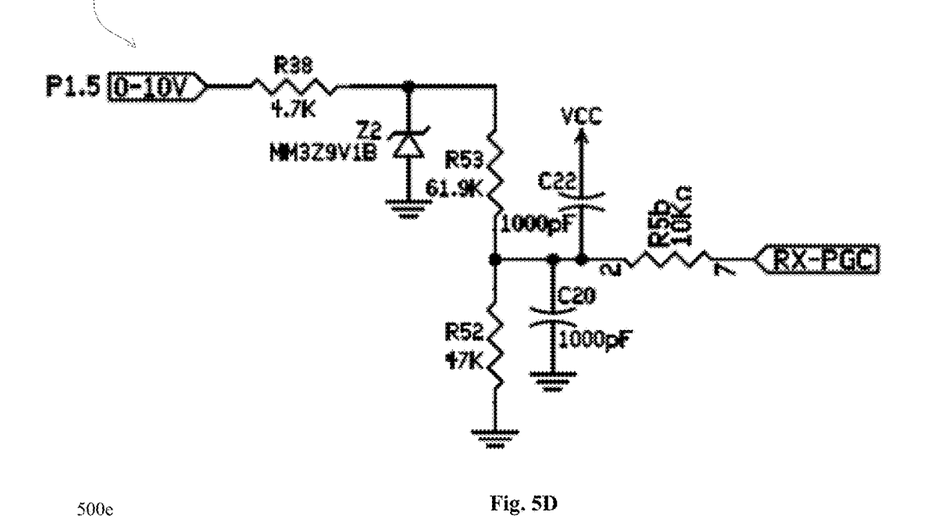
Figure 5E:
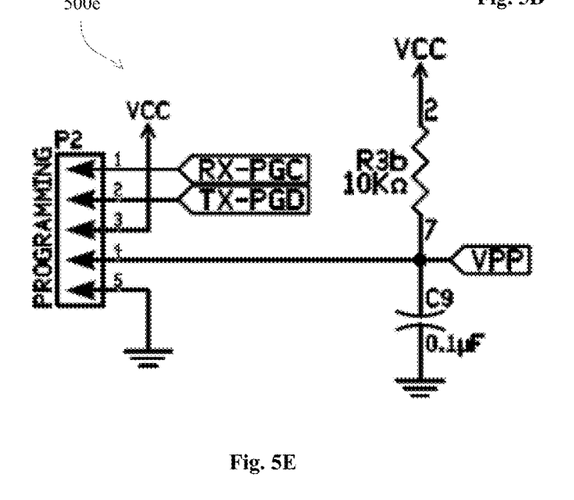
Figure 5F:
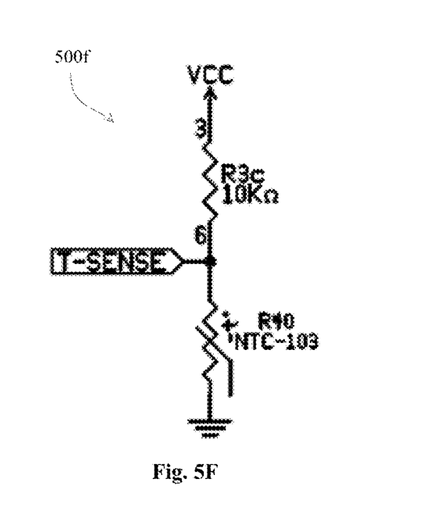
Figure 5G:
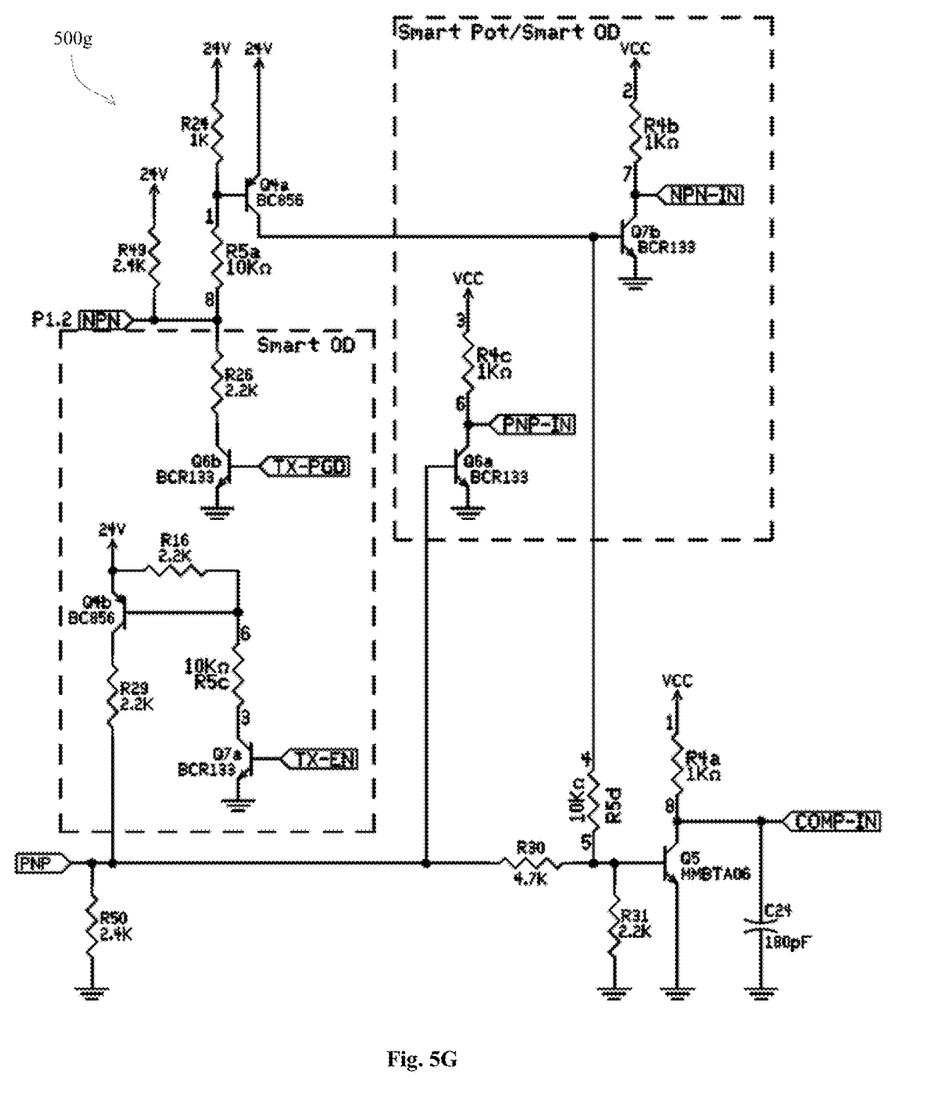
Figure 5H:
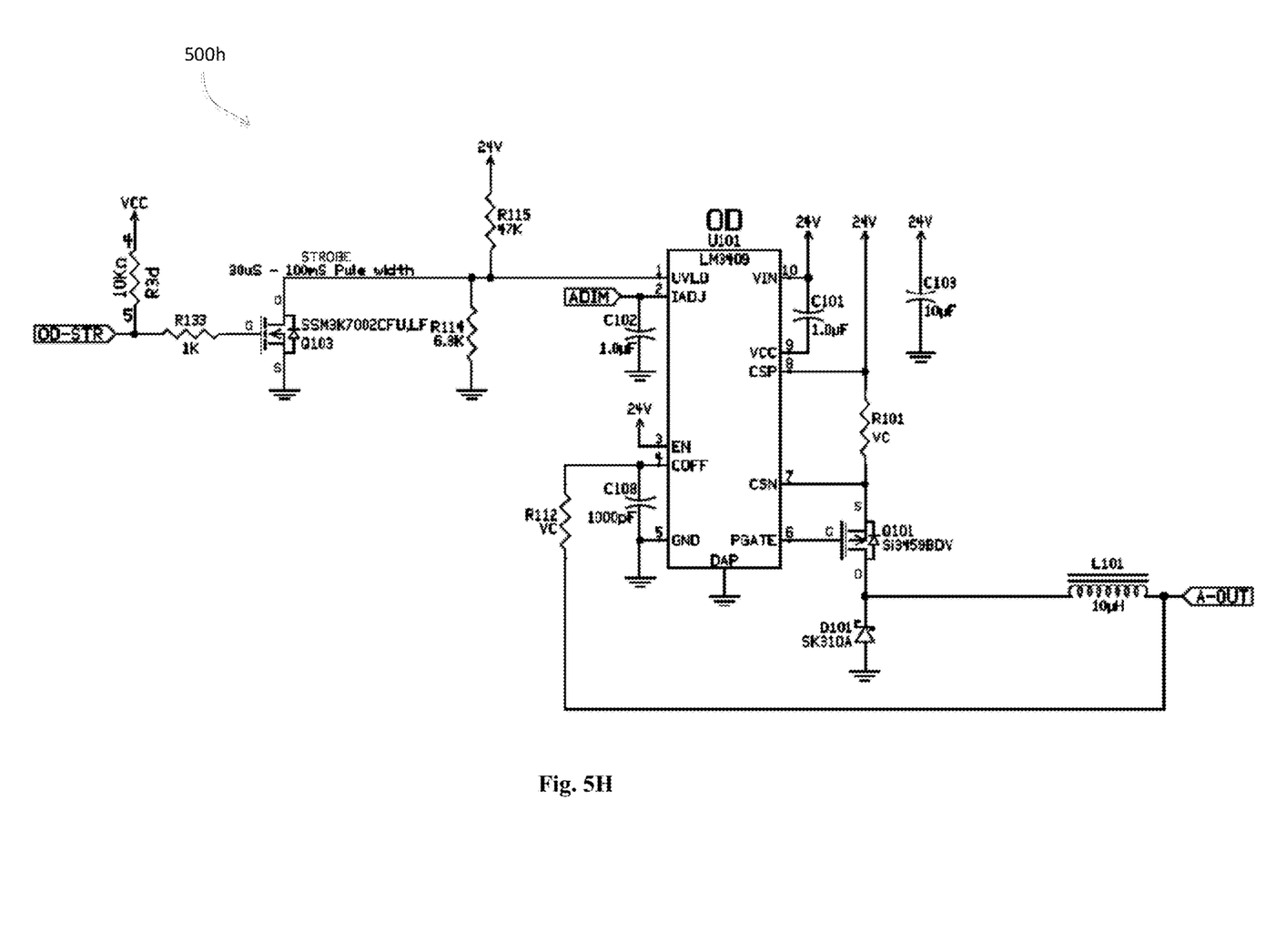
Figure 5J:
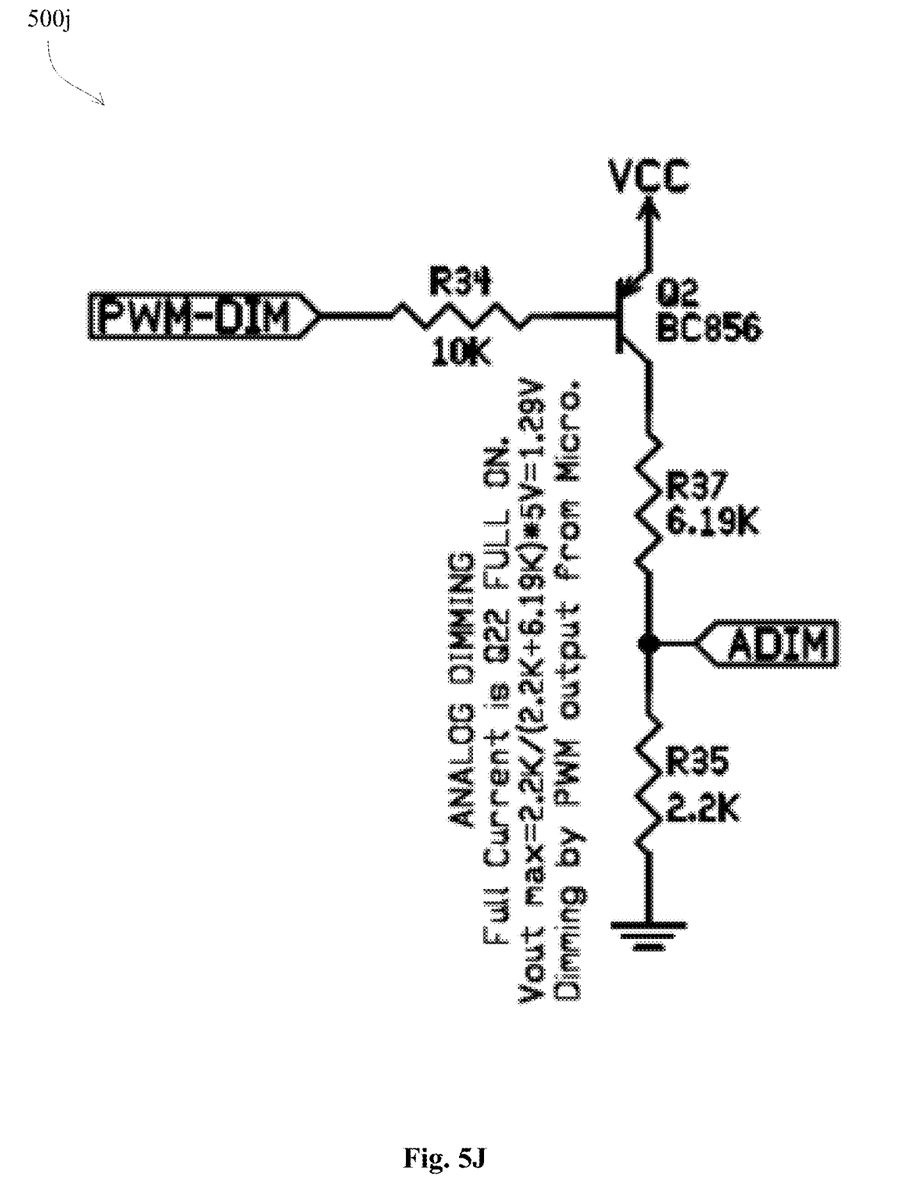
Figure 5K:
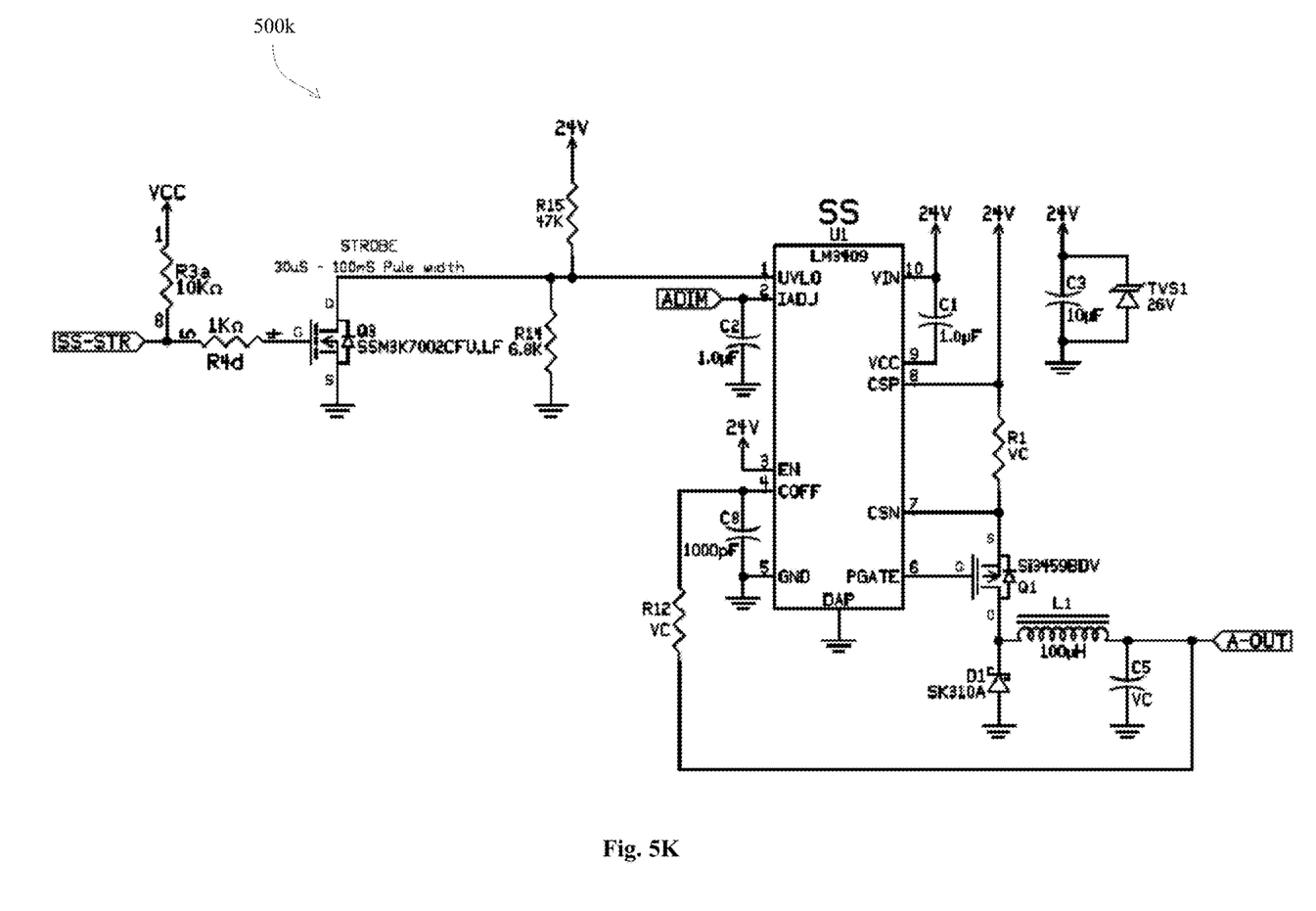

With reference to FIG. 4, a web-scanning, polarized illumination source 400 may include at least one linear, high power light source (e.g., L.E.D.) illumination bar 410, a linear reflector 425, a linear wire grid polarizer 420, and at least one high temperature focusing lens 435 to create a planar web-scanning polarized light emission 445. The illumination source 400 may also include a cover 440. The illumination bar 410, the linear reflector 425, the linear wire grid polarizer 420, the focusing lens 435 and the cover may secured in position relative one another via a housing 405.

Turning to FIGS. 5A-H, J and K, a multi-drive circuit 500a-h, j and k may be configured to provide a first range of illumination source drive current and a second range of illumination source driver current. The first range of illumination source drive current and the second range of illumination source driver current may be independent of one another. Alternatively, or additionally, the first range of illumination source drive current and the second range of illumination source driver current may at least partially overlap with one another.

In any event, the circuit labeled SS (steady state) may define a continuous current circuit. The circuit labeled OD (over-drive) may define a pulsed high current drive circuit. Together, the SS circuit and the OD circuit may define a multi-drive circuit. The microcontroller (U2) may control how the SS and OD circuits function.

Typically, LEDs may be powered with a continuous constant current source and may operate within an operating current specified by an associated LED manufacturer. If more light output is required for a particular machine vision system, additional LEDs may be wired in series and/or in parallel to define a series (or parallel) string. LEDs wired in series may have a common current flowing through each. Voltage drop across a series string of LEDs may increase proportionally with each additional LED. A maximum number of LEDs in series may depend on an associated current source's maximum voltage rating. A brightness (output power) in a LED series string may be controlled via a current source being adjusted, for example, from zero current (LEDs off) to maximum current (full brightness). If additional light output is required, and a maximum number of LEDs has been reached due to the voltage limitation, multiple series strings of LEDs can be connected in parallel as long as the maximum current of the current source has not been exceeded.

A maximum current that may flow through an LED may be a function of how long the LED is turned on (or energized) relative to how long the LED is turned off (or de-energized) on a periodic basis. Turning on and off is often referred to as a duty cycle, and may be expressed as a percentage. Typically, the lower the duty cycle, the higher the current the LED can handle.

Some machine vision applications do not require continuous lighting, therefore, associated LEDs can be turned on (strobed) for a duration of time less than being continuously on. Continuously on may be considered 100% on. Accordingly, an application that does not require constant on, can range from zero percent on (LEDs off) to an infinite number of on durations (i.e., 10%, 38%, 62%, etc.). An advantage of turning on the LEDs for only the required duration may be that a higher current can be used in the LED strings, which may result in a brighter light output being realized or fewer LEDs required for a same light brightness.

A circuit used to provide power to the LEDs (drive current) can be of several circuit configurations: continuous current; strobed current at a higher current than specified for a shorter duration; periodic, with an adjustable duty cycle and higher current than specified; and multi-drive, a combination of one or more of the above listed circuit configurations, which can be selected by the user or automatically configured by the system for optimum performance.

The polarized electromagnetic radiation of the present disclosure may be used for illumination in machine vision applications. The polarized electromagnetic radiation of the present disclosure may be used for polarized light in line scanning applications. The polarized electromagnetic radiation of the present disclosure may be used for polarized light in long source arrays with narrow apertures for web-scanning applications. The polarized electromagnetic radiation of the present disclosure may include nano-wire diffraction grids as the polarizing medium. The polarized electromagnetic radiation of the present disclosure may include a polarizing-transmission coating system on a planar transparent material to polarize light. The polarized electromagnetic radiation of the present disclosure may include a reflective means of polarizing light. The polarized electromagnetic radiation of the present disclosure may include a prismatic refraction medium to spread multiple line scanning zones by color spectra and polarize light for line scanning. The polarized electromagnetic radiation of the present disclosure may include electrically stimulated photochromic thin film coatings which, for example, may selectively phase shift (e.g., rotate) electric vector components of polarized illumination. The polarized electromagnetic radiation of the present disclosure may include thin-film optical filters to control a spectra of polarized light source for machine vision purposes.

A polarizing illumination system of the present disclosure may include invisible (to a human eye) and polarized illumination sources to react with special inks to identify secure materials by a special camera modified to read wavelengths either longer or shorter than human vision can detect. The polarized electromagnetic radiation of the present disclosure may include a feedback control link which may, for example, enable an illumination system to employ control over illumination intensity, spectral properties, duration and frequency of illumination (e.g., flashing control), or plane of polarization.

A high power, linear, focused, and polarized illumination system is provided that may include materials which may sustain continuous operation at source-light power densities greater than 100 W/Meter-Squared. The polarized electromagnetic radiation of the present disclosure may include a wire grid polarizer between, for example, 2-symmetrical lenses to reduce optical aberration, control focusing, and beam collimation in the illumination source. The polarized electromagnetic radiation of the present disclosure may include a narrow, optimally shaped reflective cavity to focus and collimate into narrow (thin) but wide-aperture a polarized beam for high speed webscanning applications.

This detailed description is to be construed as exemplary only and does not describe every possible embodiment, as describing every possible embodiment would be impractical, if not impossible. One may be implement numerous alternate embodiments, using either current technology or technology developed after the filing date of this application.

What is claimed is:

1. A machine vision system, comprising:
   at least one illumination source for emitting light;
   a multi-drive circuit connected to the at least one illumination source;
   a controller configured to control the multi-drive circuit, wherein the multi-drive circuit includes a steady state circuit to provide a continuous current to the at least one illumination source when the controller turns on the steady state circuit, and wherein the multi-drive circuit includes an over-drive circuit to provide a pulsed current to the at least one illumination source when the controller turns on the overdrive circuit;
at least one polarizer for polarizing the light emitted from the at least one illumination source;
at least one optical element for focusing the light emitted from the at least one illumination source; and
at least one light detector, wherein the at least one light detector is configured to detect the polarized light reflected from an optical code being read by the machine vision system.

2. The machine vision system of claim 1, wherein the controller is configured to control at least one of: an illumination intensity of the at least one illumination source, a spectral property of the at least one illumination source, a duration of the at least one illumination source, a frequency of illumination of the at least one illumination source, a flashing frequency of the at least one illumination source, or a plane of polarization of the at least one illumination source.

3. The machine vision system of claim 1, which includes polarized light in long source arrays with narrow apertures configured as a web-scanner.

4. The machine vision system of claim 1, wherein the controller is configured to control an illumination intensity of the at least one illumination source by selectively turning on the steady state circuit to provide a first illumination intensity and turning on the over-drive circuit to provide a second illumination intensity which defines a higher illumination intensity than the first illumination intensity.

5. The machine vision system of claim 1, wherein the at least one polarizer includes a polarizing-transmission coating on a planar transparent material.

6. The machine vision system as in claim 1, wherein the at least one polarizer includes a reflective means of polarizing light.

7. The machine vision system of claim 6, wherein the at least one optical element includes a prismatic refraction medium to spread multiple line scanning zones by color spectra and polarize light for line scanning.

8. The machine vision system of claim 1, wherein the controller is configured to provide a first range of illumination source drive current and a second range of illumination source driver current, and wherein the controller is configured to control an illumination intensity of the at least one illumination source based on the first and second ranges of illumination source drive current.

9. The machine vision system of claim 1, wherein the controller is configured to provide a first range of illumination source drive current and a second range of illumination source driver current.

10. An illumination source for machine vision systems, comprising:
at least one illumination source for emitting light;
a controller configured to control a multi-drive circuit, wherein the multi-drive circuit includes a steady state circuit to provide a continuous current to the at least one illumination source when the controller turns on the steady state circuit, and wherein the multi-drive circuit includes an over-drive circuit to provide a pulsed current to the at least one illumination source when the controller turns on the overdrive circuit;
at least one polarizer for polarizing the light emitted from the at least one illumination source;
at least one optical element for focusing the light emitted from the at least one illumination source; and at least one light detector, wherein the at least one light detector is configured to detect the polarized light reflected from an optical code being read by the machine vision system.

11. The illumination source for machine vision systems of claim 10, wherein the at least one illumination source emits light that is invisible to a human eye.

12. The illumination source for machine vision systems of claim 11, wherein the at least one polorizer is configured to polarize the light emitted by the at least one illumination source to react with ink.

13. The illumination source for machine vision systems of claim 12, configured within a machine vision system and further comprising:
a camera that detects wavelengths of light that are either longer or shorter than a human eye can detect.

14. An illumination source for machine vision systems, comprising:
at least one illumination source for emitting light;
a multi-drive circuit connected to the at least one illumination source;
a controller configured to control the multi-drive circuit, wherein the multi-drive circuit includes a steady state circuit to provide a continuous current to the at least one illumination source when the controller turns on the steady state circuit, and wherein the multi-drive circuit includes an over-drive circuit to provide a pulsed current to the at least one illumination source when the controller turns on the overdrive circuit;
at least one polarizer for polarizing the light emitted from the at least one illumination source;
at least one optical element for focusing the light emitted from the at least one illumination source;
at least one feedback control link which enables an associated illumination system to control at least one of: an illumination intensity of emitted light, a spectral property of emitted light, a duration of an on-time of the at least one illumination source, a frequency of flashing on and off of the at least one illumination source, or a plane of polarization of emitted light; and
at least one light detector, wherein the at least one light detector is configured to detect the polarized light reflected from an optical code being read by the machine vision system.

15. The illumination source for machine vision systems of claim 14, configured as a high power, linear, focused, and polarized illumination system.

16. The illumination source for machine vision systems of claim 15, further comprising:
materials which sustain continuous operation at source-light power densities greater than 100 W/Meter-Squared.

17. The illumination source for machine vision systems of claim 14, wherein the at least one polarizer includes a wire grid polarizer.

18. The illumination source for machine vision systems of claim 17, wherein the at least one polarizer is positioned between a first symmetrical lens and a second symmetrical lens.

19. The illumination source for machine vision systems of claim 18, configured to reduce optical aberration, control focusing, and beam collimation of light emitted from the at least one illumination source.

20. The illumination source for machine vision systems of claim 14, further comprising:

a narrow shaped reflective housing configured to focus and collimate light emitted from the at least one illumination source into a narrow band to produce a wide-aperture polarized beam of light for high speed web scanning.

* * * * *